United States Patent [19]

Stetter et al.

[11] Patent Number: 5,055,266

[45] Date of Patent: Oct. 8, 1991

[54] METHOD FOR DETECTING TOXIC GASES

[75] Inventors: Joseph R. Stetter, Naperville; Solomon Zaromb, Hinsdale; Melvin W. Findlay, Jr., Bolingbrook, all of Ill.

[73] Assignee: ARCH Development Corporation, Argonne, Ill.

[21] Appl. No.: 499,202

[22] Filed: Mar. 23, 1990

Related U.S. Application Data

[63] Continuation of Ser. No. 585,721, Mar. 2, 1984, abandoned.

[51] Int. Cl.$^5$ .................... G01N 27/00; G01N 31/12; G01N 27/16; G01N 25/22

[52] U.S. Cl. ........................................ 422/83; 422/94; 422/95; 422/98; 436/106; 436/109; 436/120; 436/122; 436/124; 436/155; 436/159; 204/153.1; 204/400; 204/431; 73/23.31; 73/25.01

[58] Field of Search .................. 422/83, 94, 95, 98; 436/106, 109, 119, 120, 122, 124, 133, 155, 159; 204/153.1, 400, 431, 432; 73/23.31, 25.01

[56] References Cited

U.S. PATENT DOCUMENTS

| | | | |
|---|---|---|---|
| 2,768,069 | 10/1956 | Thompson | 73/23.31 |
| 2,805,134 | 9/1957 | Strange | 73/25.01 |
| 3,200,011 | 8/1965 | Baker | 422/94 X |
| 3,445,757 | 5/1969 | Krucoff | 324/464 |
| 3,607,084 | 9/1971 | Mackey et al. | 436/133 |
| 3,713,773 | 1/1973 | Fontijn et al. | 436/117 |
| 3,791,936 | 2/1974 | Pebler et al. | 422/94 |
| 3,961,248 | 6/1976 | Kawamura | 422/98 |
| 3,977,836 | 8/1976 | Matsuda et al. | 422/83 |
| 4,036,592 | 7/1977 | Brown et al. | 436/133 |
| 4,092,232 | 5/1978 | Zetter | 204/408 |
| 4,111,658 | 9/1978 | Firth et al. | 422/98 |
| 4,127,462 | 11/1978 | Blurton et al. | 204/412 |
| 4,140,106 | 2/1979 | Kirmaier | 73/27 R |
| 4,170,455 | 10/1979 | Henrie | 422/94 |
| 4,203,726 | 5/1980 | Patterson | 73/23 |
| 4,242,302 | 12/1980 | Kitamura et al. | 422/94 |
| 4,246,228 | 1/1981 | Jones et al. | 422/94 |
| 4,266,196 | 5/1981 | Kawazoe et al. | 324/464 |
| 4,283,256 | 8/1981 | Howard et al. | 204/1 T |
| 4,305,724 | 12/1981 | Micko | 422/94 |
| 4,326,927 | 4/1982 | Stetter et al. | 204/412 |
| 4,364,810 | 12/1982 | Razumney | 204/431 |
| 4,368,431 | 1/1983 | Rohr et al. | 324/464 |
| 4,457,954 | 7/1984 | Dabill et al. | 422/98 |
| 4,458,242 | 7/1984 | Kusanagi et al. | 340/634 |
| 4,475,378 | 10/1984 | Boutonnate et al. | 340/634 |
| 4,560,585 | 12/1985 | Khilnani | 422/98 |

FOREIGN PATENT DOCUMENTS

| | | | |
|---|---|---|---|
| 0018871 | 11/1980 | European Pat. Off. | 422/94 |
| 2812613 | 9/1979 | Fed. Rep. of Germany . | |
| 2451581 | 2/1980 | France . | |
| 0134697 | 10/1979 | Japan | 422/98 |
| 0164947 | 12/1981 | Japan | 422/94 |
| 0069239 | 4/1982 | Spain | 422/98 |
| 0750364 | 7/1980 | U.S.S.R. | 204/400 |
| 2017315 | 10/1979 | United Kingdom . | |
| 2098741 | 11/1982 | United Kingdom . | |
| 2099588 | 12/1982 | United Kingdom . | |
| 0098716 | 1/1984 | United Kingdom . | |

OTHER PUBLICATIONS

Interscan Corporation, "VIKANE" Monitor.
Preparation of Fast Detecting SnO$_2$ Gas Sensors, Pink et al., Japaneses J. of App. Phys., vol. 19, No. 3, Mar. 1980, pp. 513–517.

Primary Examiner—Robert J. Warden
Assistant Examiner—Theresa A. Trembley
Attorney, Agent, or Firm—Larson & Taylor

[57] ABSTRACT

A method capable of detecting low concentrations of a pollutant or other component in air or other gas, utilizing a combination of a heating filament having a catalytic surface of a noble metal for exposure to the gas and producing a derivative chemical product from the component, and an electrochemical sensor responsive to the derivative chemical product for providing a signal indicative of the product. At concentrations in the order of about 1–100 ppm of tetrachloroethylene, neither the heating filament nor the electrochemical sensor is individually capable of sensing the pollutant. In the combination, the heating filament converts the benzyl chloride to one or more derivative chemical products which may be detected by the electrochemical sensor.

14 Claims, 4 Drawing Sheets

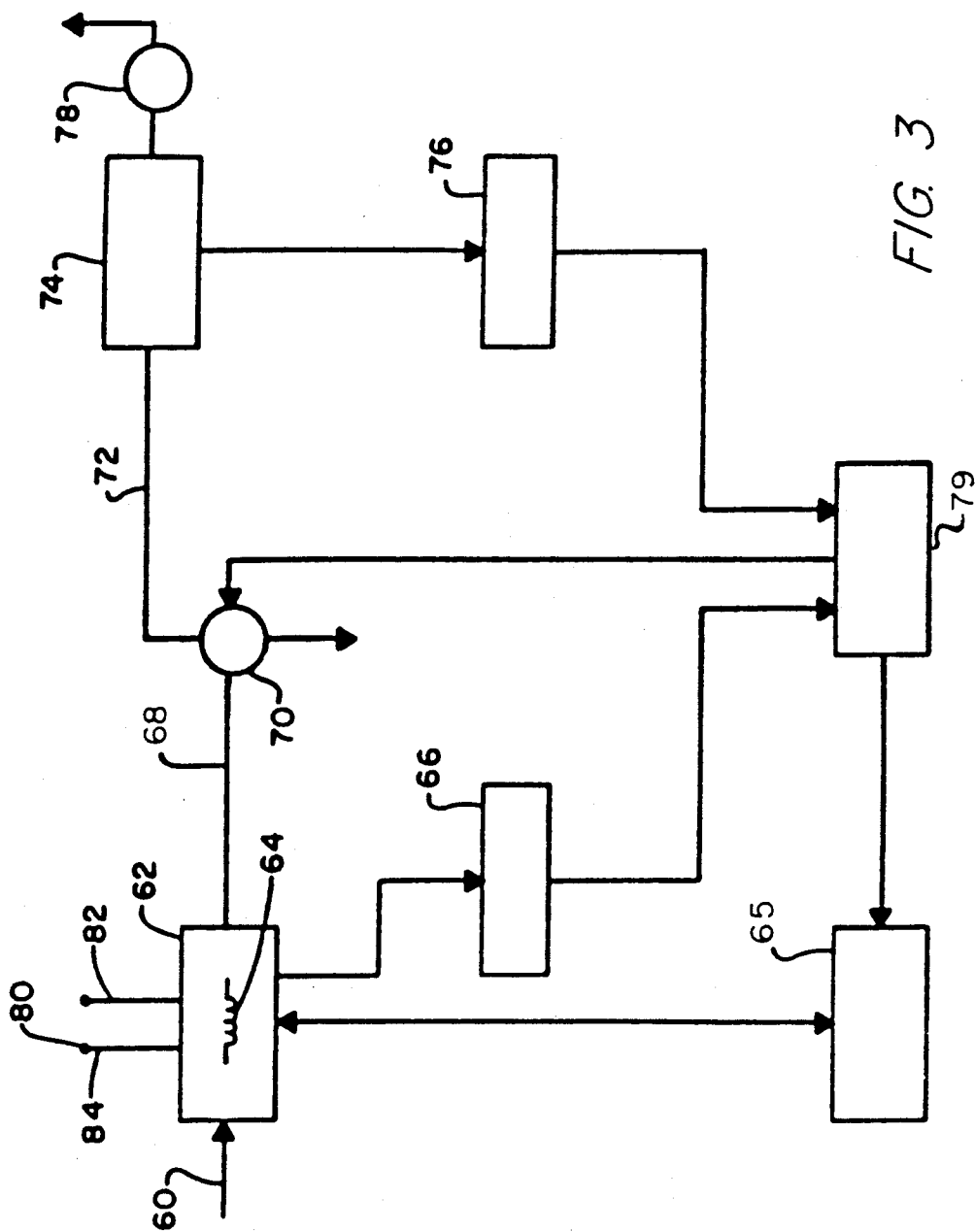

METHOD FOR DETECTING TOXIC GASES

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

This application is a continuation of application Ser. No. 585,721 filed Mar. 2, 1984, now abandoned.

BACKGROUND OF THE INVENTION

This invention relates to devices for detecting pollutants and more particularly to devices capable of detecting pollutants at relatively low concentrations in ambient gases. Electrochemical sensing devices, especially amperometric sensors such as those disclosed in U.S. Pat. Nos. 3,776,832, 4,201,634 and 4,326,927 offer the advantages of portability, real-time readout, relatively low cost, and fair sensitivity and selectivity to a few specific pollutants such as CO, $H_2S$, NO, $NO_2$, $SO_2$, hydrazine, $COCl_2$, HCN, or $Cl_2$. However, these devices are not applicable, at present, to the detection of many species that are not electrochemically active.

In detecting pollutants including toxic substances, sensing devices have usually been limited with respect to concentrations of the pollutants particularly when the pollutants are essentially not electrochemically active or have an activity difficult to detect. Below certain values of concentration, e.g., 100 ppm (parts per million) of benzyl chloride, tetrachloroethylene or the like, presently available portable devices are essentially unresponsive to the pollutant. Since some pollutants may be extremely toxic, it is important to develop devices for detecting various pollutants at low concentrations.

Accordingly, one object of this invention is a device for detecting pollutants at low concentrations in gases. Another object is an electrochemical device for detecting pollutants in ambient gases where the pollutants are essentially electrochemically inactive or have an activity difficult to detect. An additional object is a device which may be utilized as a portable instrument to survey an area or as a site monitor for a wide variety of gases. A further object is a device which is also capable of detecting pollutants at higher concentrations, at which level they may present an acute toxicity or flammability hazard.

SUMMARY OF THE INVENTION

Briefly, the invention relates to a device for detecting a pollutant in an ambient gas and comprises (1) electrical conversion means having a catalytic surface to chemically convert the pollutant (e.g., a hydrocarbon) to a derivative product (e.g., carbon monoxide) having a characteristic electrochemical activity, and (2) electrochemical sensing means responsive to that electrochemical activity and providing a signal indicative of the derivative product and thereby the original pollutant. In one embodiment, the conversion means includes a sensor responsive to higher concentrations of an electrochemically inactive pollutant, but essentially unresponsive to lower concentrations, and an electrochemical sensor responsive to the derivative product, but essentially unresponsive to the pollutant at low concentrations. The conversion means may comprise a heated filament made of or coated with a noble metal catalyst, such as Pt, Pd, Ir, Rh, Au, Ag, or an alloy or compound of one of such metals.

BRIEF DESCRIPTION OF THE DRAWINGS

FIG. 3 is a flow diagram of yet another embodiment of the invention.

DETAILED DESCRIPTION OF THE PREFERRED EMBODIMENT

The device of the invention is suitable for use in detecting at least one of a variety of pollutants or otherwise hazardous gases or vapors in ambient gas. These pollutants commonly include various organic compositions such as benzene, benzyl chloride, toluene, methane, tetrachloroethylene, tetrahydrofuran, cyclohexane and the like. It is particularly useful for detecting the presence of a pollutant such as benzyl chloride or benzene at low concentrations in the order of about 1-100 ppm where some sensing devices are inoperative. In addition, the device may be constructed of components permitting its use as a portable instrument capable of on-site detection of a pollutant and in some instances fixed site analysis of the general concentration of the pollutant.

The device includes in combination, electrical heating means having a noble metal exposed surface for chemically changing the pollutant to a derivative product having a characteristic electrochemical activity and a sensing means responsive to the electrochemical activity of the product and including signal means providing a signal indicative of the product and thereby the pollutant. The derivative product results from the chemical change in the pollutant which may occur from the oxidation or other process on the pollutant to either form electrochemical activity or change the existing activity of the pollutant. A particularly useful combination for the device includes a noble metal heating means which also operates as a sensor providing a signal at concentrations of the pollutant above about 0.1-1.0% while providing the derivative product over the overall concentration range for detection by the electrochemical sensing means. The presence or absence of the signal from the noble metal heating means in combination with the signal from the electrochemical sensing means may be used in determining the presence or absence of a pollutant and its general concentration range.

The derivative product from the pollutant exhibits a characteristic electrochemical activity which may be detected by the sensing means at levels as low as about one ppm. These products may be the oxides of carbon, sulfur, nitrogen and the like having electrochemical activity and other compositions indicative of partial oxidation or decomposition of the pollutant.

Figure 1:
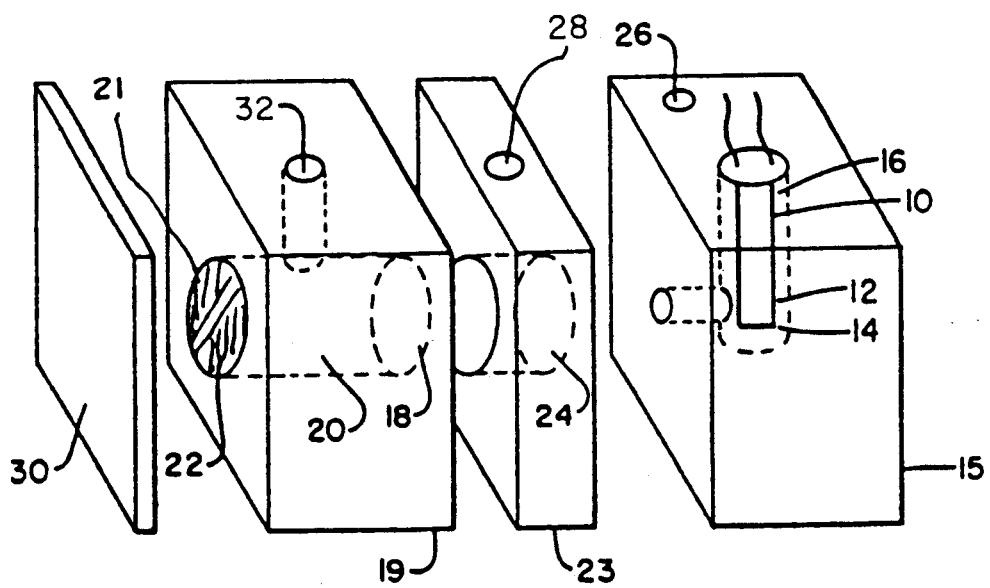
FIG. 1 is an exploded view of one embodiment of the invention.

The device of FIG. 1 includes the catalytic heating means as illustrated by a hot-wire sensor arranged to receive a sample of the ambient gas and sensing means illustrated by an electrochemical sensor arranged to receive the derivative product. The conversion means may include a signal means for providing a signal apart from the signal from the sensing means. The hot-wire sensor includes a heating means and a catalyst such as one or more of the oxidation catalysts. In general, hot-wire sensors and catalysts based on Pt, Pd, Rh and Au are particularly useful. Also useful may be catalysts comprising Ir or Ag, or various noble metal alloys, such as Pd-Ag, Pt-Rh, Pt-Ir or Au-Ag, or a compound, especially an oxide, of one of said metals. The hot wires or filaments may be either made of a pure noble metal or, preferably, be coated on a suitable baser metal or alloy. The catalysts may also be dispersed on a support such as C, Si or alumina. As the sample is exposed to the hot catalyst, it is chemically changed and preferably oxidized or decomposed to at least one derivative product which may be detected by the electrochemical sensor.

The electrochemical sensor is responsive to low levels of the derivative product and provides a signal indicative of the product and thereby the pollutant. While the electrochemical sensor is responsive to some electrochemically active substances at these low levels, its response to compounds such as benzyl chloride and the like which are not primarily characterized by electrochemical activity tends to be so limited that it may not be used for detection unless aided by one of the above-mentioned oxidation catalysts.

Suitably, the electrochemical sensor may be a constant-potential amperometric sensor. As the derivative product is sensed, a signal is generated indicative of the electrochemical activity at the "working electrode" of the sensor. In general, the hot wire sensor representing the conversion means and the amperometric chemical sensor representing the sensing means are sufficiently small that they may be built into a single unit where the derivative product from the hot wire sensor may interact with the electrochemical sensor within the same unit. Preferably, the sample is introduced into a sample channeling arrangement by which the sample is first introduced to the hot-wire sensor. The derivative product from the hot-wire sensor is then routed to the electrochemical sensor either directly, but in a controlled manner, so as to enhance the activity of said sensor by raising its temperature to a preferred value or through a baffle arrangement or other isolation system so that the electrochemical sensor need not be directly exposed to the heater of the hot-wire sensor.

In FIG. 1, an exploded view of the invention is illustrated showing a path including a baffle arrangement to isolate the electrochemical sensor from the heater of the hot-wire sensor and thereby reduce the possibility of damage to the electrochemical sensor.

The inventive device includes electrical heating means with a noble metal surface exposed to the gas for heating the gas and catalyzing the combustion of the pollutant to provide a derivative product having a characteristic electrochemical activity and electrochemical sensing means responsive to that activity for providing a signal indicative of that activity. As illustrated in FIG. 1, the heating means is provided by a filament 10 composed of a heating element core 12 and a noble metal surface 14 mounted in a reaction chamber 16 of block 15. A sensing element 18 is mounted in chamber 20 of block 19 for detecting the electrochemical activity of the product derived from the combustion of the pollutant. A reference electrode 22 and a counter electrode 21 are also provided. Blocks 15 and 19 are joined by block 23 with chamber 24. Inlet 26, outlet 28 and chambers 16 and 24 provide channeling means for exposing the gas to the heating filament 10 and the derivative product to the sensing element 18. Closure member 30 provides sealing of chamber 20. A pluggable opening 32 above chamber 20 permits introduction of electrolyte into the electrochemical sensor.

Figure 2:
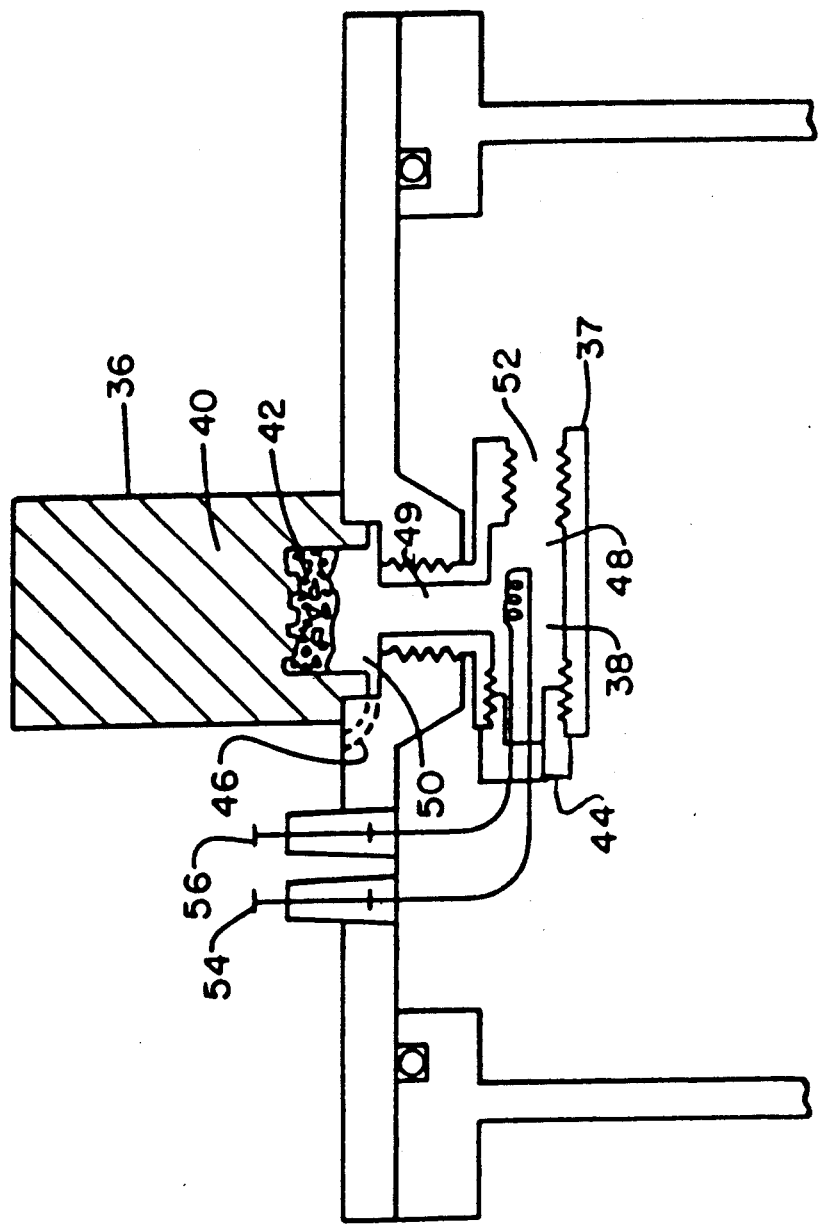
FIG. 2 is a cross-sectional view of yet another embodiment of the invention.

In another embodiment of the invention, shown in FIG. 2, a diffusion-type electrochemical sensor is used to detect concentrations of 0-2.4% methane in air by preexposing any ambient gas diffusing or convecting towards said sensor to an iridium-coated filament heated to a temperature of 300°-600° C. and preferably 400°-500° C. The filament is made preferably of a metal or alloy of relatively high resistivity having a coefficient of thermal expansion close to that of iridium, e.g., commercial grade titanium. By adjusting the filament length and cross-section to yield a resistance of about 2,000 ohms and temperature of 400°-500° C. when heated by a current of about 10 milliamperes, it becomes possible to achieve a low-power low-current-drain methane detector suitable for intrinsically safe mine-monitoring applications.

In FIG. 2 the device 36 includes heating filament 38 mounted in housing 37 with electrochemical sensing element 40 hidden from direct exposure to filament 38 by barrier 42 of glass wool or other suitable porous material. In FIG. 2, inlet 52, vent 46, and channels 48, 49 and 50 provide channeling of the gas and derivative product. A source of electrical current is provided by leads 54 and 56 passing through a ceramic plug 44 to filament 38.

The heating of the iridium-coated filament of FIG. 2 is preferably governed by a temperature controller, such as that shown in the block diagram of FIG. 3. To further reduce the heating power requirements, the filament may be heated in intermittent pulses, e.g., in pulses of 0.5 to 3 seconds' duration every 10 seconds. In general, the response time of the device is less than about 20 seconds. The heating pulses are sufficient to bring the peak filament temperature up to the range of 400°-500° C.

It is noteworthy that electrochemical sensors when used by themselves such as that used in the device of FIG. 2, do not usually respond to methane even in concentrations as high as 100%. Yet the signals obtained with the heated iridium filament permit easy measurement of methane concentrations as low as 0.05% or less.

As an illustration of the general flow diagram associated with the detection process, FIG. 3 illustrates an arrangement where the derivative product may be automatically routed through a multipath solenoid valve or other diversion means to either the electrochemical sensor or removed from the device before exposure to the sensor depending on the concentration levels. In this flow arrangement, the signal from the hot-wire sensor may serve to indicate the presence of the pollutant at a concentration above about 0.5-1.0% and may be used to direct the flow of derivative product away from the device to avoid the possible effects of an excessive concentration of certain pollutants on the electrochemical sensor.

When no signal from the hot-wire sensor is provided, the flow pattern will be used to direct the derivative product to the electrochemical sensor and its signal will provide an indication of the presence of the derivative product and thereby the pollutant. With a combination of signals, the presence of the pollutant and its concentration may be determined.

The general flow pattern of the gas and derivative product are illustrated in FIG. 3. As illustrated, a gas sample is admitted via line 60 to conversion chamber 62 having filament 64 whose temperature is controlled by controller 65. Signal indicating means is provided by indicator 66 to provide any signal available from filament 64. The derivative product is channeled via line 68, valve 70 and line 72 to the electrochemical sensor 74 having a signal indicator 76. Pump 78 provides the suction and determines the flow rate within the device. Controller 65 and valve 70 are governed by a microprocessor (computer/controller) 79 which receives the signals from indicator 66 and 76.

As an illustration of the representative performance of the above-disclosed embodiments, FIG. 4 provides response curves for benzene. In general, benzene is not readily detected on electrochemical sensors at ppm levels and is further essentially undetectable by a hot-wire sensor at ppm levels. However, by combining the two different sensors, it is possible to produce signals indicative of the presence of benzene at a concentration of less than 100 ppm level in air. While benzene at such levels is not detectable by hot-wire or heated semiconductor sensors, the heated catalytic surface of such sensors or other noble metal-coated filaments converts the benzene to one or more oxides of carbon or degradation products which are then detected by the electrochemical sensor.

Figure 4A:
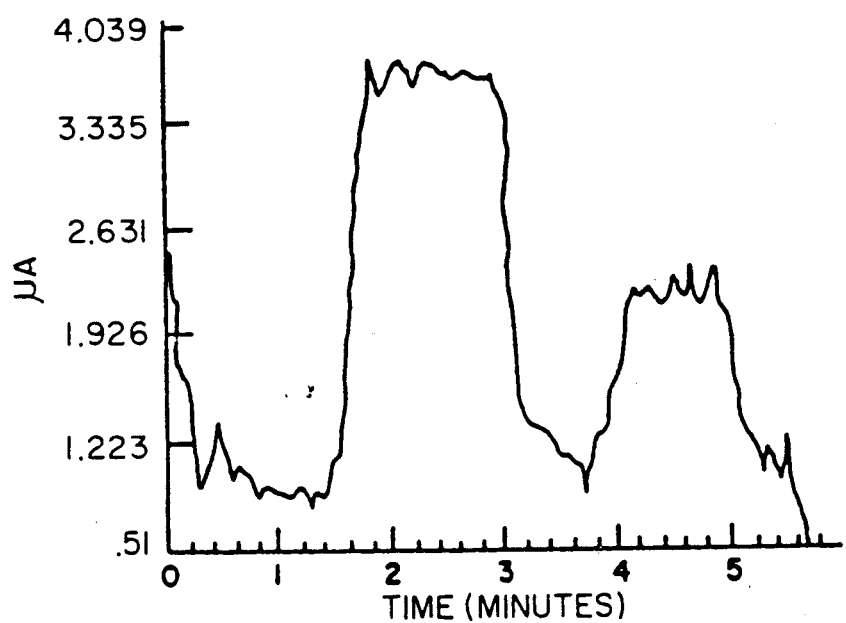
FIGS. 4(a)-(c) show representative response curves for benzene from devices constructed according to the invention.
Figure 4B:
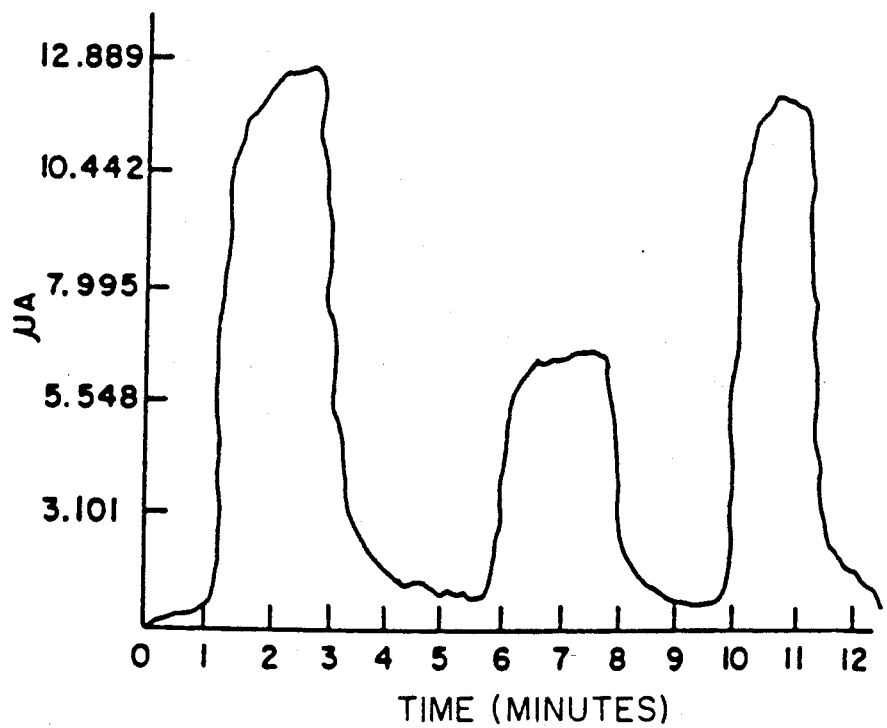
Figure 4C:
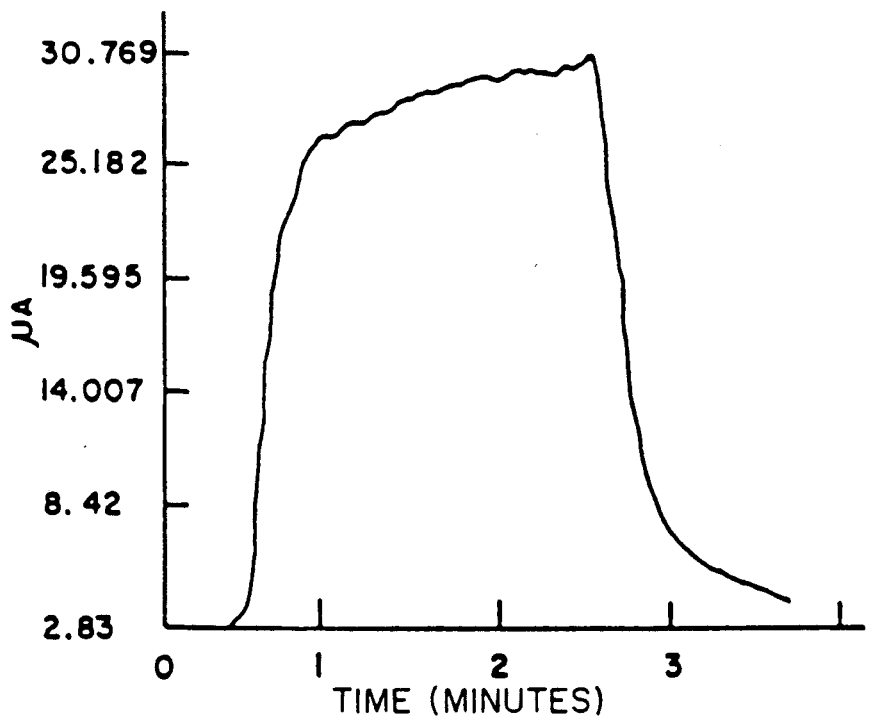

In FIG. 4A, the heated filament was made of a fine platinum wire (0.08 millimeter in diameter) similar to that used in hot-wire flammable gas sensors, heated to a temperature of about 1000° C. The two humps starting at about 1.5 minutes and 4 minutes correspond to exposure to samples of 200 ppm and 50 ppm of benzene, respectively. In FIG. 4B, a commercial tin oxide semiconductor sensor, heated to about 300° C., was used as a conversion means. The three humps starting at about 1 minute, 6 minutes, and 10 minutes correspond to samples of 200 ppm, 50 ppm, and 200 ppm of benzene, respectively. In FIG. 4C, the conversion device consisted of a fine (0.08 millimeter in diameter) gold filament heated to 950°±50° C., and the hump starting at about 0.6 minute was due to a sample of 200 ppm of benzene. The same electrochemical sensor, comprising a platinum black sensing electrode at a potential of about 1.1 volt relative to the standard reversible hydrogen electrode, was used in all three cases. A comparison of the ordinates of FIGS. 4A, B, and C shows that the heated tin oxide yields an approximately three to four times higher response than the platinum filament, but that the gold filament yields a three-fold higher response than the tin oxide and a ten times higher response than the platinum.

Other representative compounds which do not appear to be detected by either type of sensor independently but are by the two sensors in combination at concentrations of about 100 ppm or less are benzyl chloride and tetrachloroethylene.

The following example is provided for illustrative purposes and is not intended to be restrictive as to the scope of the invention:

EXAMPLE I

A sample of air containing 200 ppm of tetrachloroethylene was tested in an apparatus having a catalytic bead sensor available from Rexnord Corporation of Sunnyvale, Calif., and a Pt-catalyzed CO filament available from Energetics Science of Hawthorne, New York. The sample was tested with each element operating separately. Observed currents from each sensor operating separately were indistinguishable from normal noise levels. In another test, a similarly constructed electrochemical sensor in combination with a Pt-catalyzed CO filament was used for an air sample containing only 20 ppm tetrachloroethylene. A signal of about 0.3 microamps was observed for the combination of sensors as compared to a value of less than 0.2 (noise level) microamps without the filament.

As described above, the invention provides a useful device for detecting a gas, vapor, chemical pollutant or other component in a gaseous medium and is capable by a combination of a catalytic heating element and an electrochemical sensor of detecting the component at low concentrations.

The foregoing description of embodiments of the invention has been presented for purposes of illustration and description. It is not intended to be exhaustive or to limit the invention to the precise form disclosed, and obviously many modifications and variations are possible in light of the above teaching.

The embodiments of the invention in which an exclusive property or privilege is claimed are defined as follows:

1. A method for detecting a gas, vapor, chemical pollutant or other component of interest in a gaseous medium said method comprising:
    exposing a noble metal-containing catalytic surface of an electrical heating element to a sample gaseous medium including a component of interest so as to heat the component and catalytically produce a product which is not heat and which is a derivative chemical product of said component not present in said sample gaseous medium, the derivative chemical product having a characteristic electrochemical activity capable of causing an electrochemical sensor to produce a corresponding electrical output signal, and
    determining the amount of the component of interest in the original sample gaseous medium by determining electrochemically, using an electrochemical sensor and based on the electrochemical activity of the derivative chemical product sensed by said electrochemical sensor, the amount of the derivative chemical product produced as the derivative chemical product leaves said heating element.

2. The method of claim 1 further comprising exposing said gaseous medium to at least one further, different catalytic surface.

3. The method of claim 1 further comprising passing an electrical current through said heating element and measuring the said signal produced in response thereto.

4. The method of claim 3 further comprising interrupting the electrical current passing through said heating means.

5. The method of claim 4 further comprising interrupting said current to generate heat pulses of a predetermined duration at predetermined time intervals.

6. The method of claim 1 wherein the catalyst used includes Pt or a compound thereof.

7. The method of claim 1 wherein the catalyst used includes Au or a compound thereof.

8. The method of claim 1 wherein the catalyst used includes Ir or a compound thereof.

9. The method of claim 1 wherein the catalyst used includes Pd or a compound thereof.

10. The method of claim 1 wherein the catalyst used includes Rh or a compound thereof.

11. The method of claim 1 wherein the catalyst used includes a mixture of Pd and Ag or compounds thereof.

12. The method of claim 3 comprising exposing said sample gaseous medium to a plurality of different catalytic surfaces.

13. The method of claim 3 further comprising using an electrical heating element having a core material with an electrical resistivity above that of the noble metal and with a coefficient of thermal expansion comparable to that of the noble metal.

14. The method of claim 1 wherein an electrochemical sensing means is used in determining the amount of the component of interest, said method further including channeling said gaseous medium to said heating element and channeling said product to said electrochemical sensing means while preventing direct exposure of said sensing means to said heating element.

* * * * *